(12) United States Patent
Dailey

(10) Patent No.: US 9,814,650 B1
(45) Date of Patent: Nov. 14, 2017

(54) SELF-DISINFECTING MEDICATION VIAL CAP ASSEMBLY

(71) Applicant: Stephen Dailey, Shreveport, LA (US)

(72) Inventor: Stephen Dailey, Shreveport, LA (US)

( * ) Notice: Subject to any disclaimer, the term of this patent is extended or adjusted under 35 U.S.C. 154(b) by 351 days.

(21) Appl. No.: 14/691,144

(22) Filed: Apr. 20, 2015

(51) Int. Cl.
*A61M 5/32* (2006.01)
*A61J 1/14* (2006.01)
*A61M 39/04* (2006.01)
*A61J 1/20* (2006.01)
*A61M 39/00* (2006.01)

(52) U.S. Cl.
CPC ............ *A61J 1/1443* (2013.01); *A61J 1/1406* (2013.01); *A61J 1/1412* (2013.01); *A61J 1/2096* (2013.01); *A61M 2039/0081* (2013.01); *A61M 2039/047* (2013.01)

(58) Field of Classification Search
CPC ...... A61J 1/1443; A61J 1/1406; A61J 1/1412; A61J 1/2096; A61M 2039/0081; A61M 2039/047
USPC ................................. 604/415; 215/249, 232
See application file for complete search history.

(56) References Cited

U.S. PATENT DOCUMENTS

| | | | |
|---|---|---|---|
| 2,186,888 A | 1/1940 | Tullar et al. | |
| 2,459,304 A * | 1/1949 | Blank | B65D 51/002 215/247 |
| 3,352,762 A | 11/1967 | Weiner | |
| 4,880,602 A | 11/1989 | Al-Sioufi | |
| 5,067,948 A | 11/1991 | Haber et al. | |
| 5,279,576 A | 1/1994 | Loo et al. | |
| 5,332,113 A * | 7/1994 | Kusler, III | A61J 1/1406 215/232 |
| 5,667,094 A * | 9/1997 | Rapchak | B65D 43/162 215/306 |
| 6,001,087 A | 12/1999 | Zurcher | |
| 7,673,763 B1 * | 3/2010 | Oh | B65D 41/0471 215/222 |
| 7,780,794 B2 | 8/2010 | Rogers et al. | |
| 7,985,302 B2 | 7/2011 | Rogers et al. | |
| 8,057,762 B2 | 11/2011 | Kacian et al. | |
| 8,206,514 B2 | 6/2012 | Rogers et al. | |
| 8,685,347 B2 | 4/2014 | Kacian et al. | |
| 2013/0224866 A1 | 8/2013 | Lurvey et al. | |

* cited by examiner

*Primary Examiner* — Tatyana Zalukaeva
*Assistant Examiner* — Andrew J Mensh
(74) *Attorney, Agent, or Firm* — R. Keith Harrison

(57) ABSTRACT

A self-disinfecting medication vial cap assembly for a medication vial includes a needle-penetrable assembly base configured for attachment to the medication vial; an assembly cap carried by the assembly base, the assembly base and the assembly cap having a cap interior and the assembly cap positional between closed and open positions; a rupturable antiseptic pouch attached to the assembly base and the assembly cap in the cap interior; and an antiseptic contained in the antiseptic pouch. The antiseptic pouch remains intact in the closed position of the assembly cap. The antiseptic pouch ruptures and the antiseptic is discharged onto the assembly base upon movement of the assembly cap from the closed position to the open position.

20 Claims, 4 Drawing Sheets

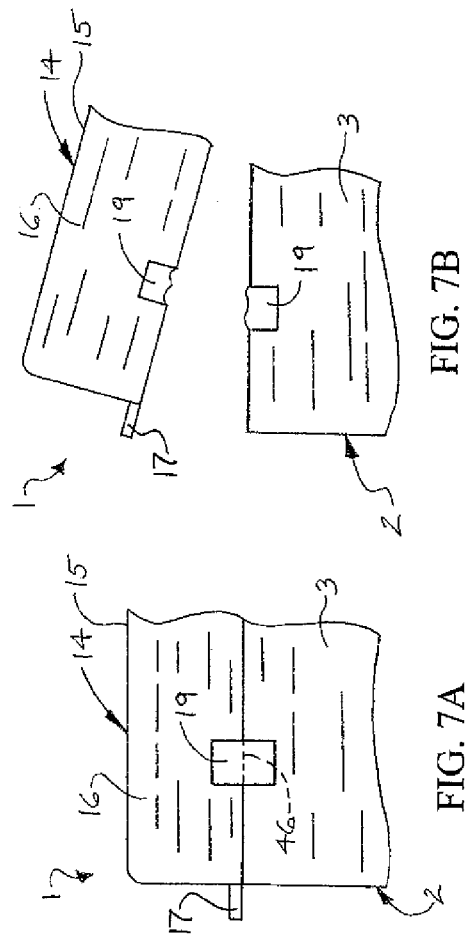
FIG. 7A
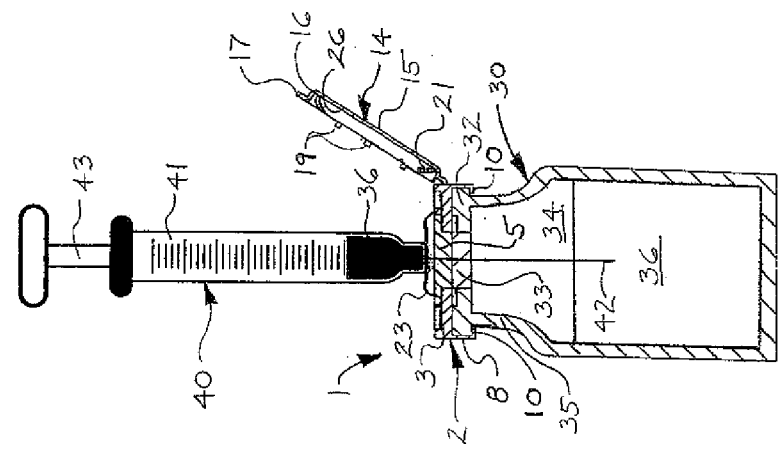
FIG. 7B
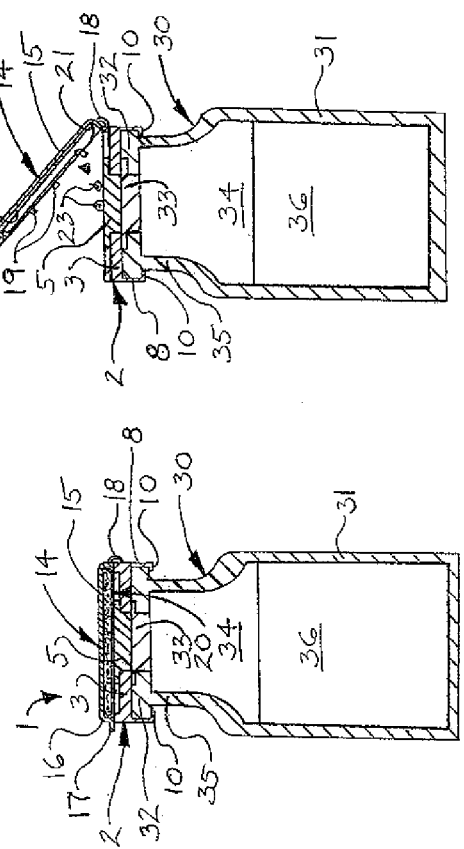
FIG. 8
FIG. 9
FIG. 10

250 # SELF-DISINFECTING MEDICATION VIAL CAP ASSEMBLY

FIELD

Illustrative embodiments of the disclosure generally relate to medication vials which contain medication typically for injection into a patient. More particularly, illustrative embodiments of the disclosure relate to a self-disinfecting medication vial cap assembly which fits on a medication vial and releases an antiseptic upon opening for sterile insertion of a syringe needle into and removal of the syringe needle from the medication vial.

SUMMARY

Illustrative embodiments of the disclosure are generally directed to a self-disinfecting medication vial cap assembly for a medication vial. An illustrative embodiment of the self-disinfecting medication vial cap assembly includes a needle-penetrable assembly base configured for attachment to the medication vial; an assembly cap carried by the assembly base, the assembly base and the assembly cap having a cap interior and the assembly cap positional between closed and open positions; a rupturable antiseptic pouch attached to the assembly base and the assembly cap in the cap interior; and an antiseptic contained in the antiseptic pouch. The antiseptic pouch remains intact in the closed position of the assembly cap. The antiseptic pouch ruptures and the antiseptic is discharged onto the assembly base upon movement of the assembly cap from the closed position to the open position.

BRIEF DESCRIPTION OF THE DRAWINGS

Illustrative embodiments of the disclosure will now be described, by way of example, with reference to the accompanying drawings, in which:

FIG. 7A is an enlarged side sectional view of the illustrative self-disinfecting medication vial cap assembly, with an intact cap tab securing the assembly cap in the closed position on the assembly base;

FIG. 7B is an enlarged side sectional view of the illustrative self-disinfecting medication vial cap assembly with the formerly intact cap tab broken upon opening of the assembly cap on the assembly base;

FIG. 8 is a cross-sectional view of the illustrative self-disinfecting medication vial cap assembly and medication vial with the assembly cap closed on the assembly base;

FIG. 9 is a cross-sectional view of the illustrative self-disinfecting medication vial cap assembly and medication vial with the assembly cap in a partially-opened position and illustrating rupturing of the antiseptic pouch to disinfect the assembly base upon opening of the assembly cap;

FIG. 10 is a cross-sectional view of the illustrative self-disinfecting medication vial cap assembly and medication vial with the assembly cap in a fully-opened position and a syringe needle on a syringe inserted through the disinfected assembly base for removal of medication from the medication vial;

DETAILED DESCRIPTION

Figure 1:
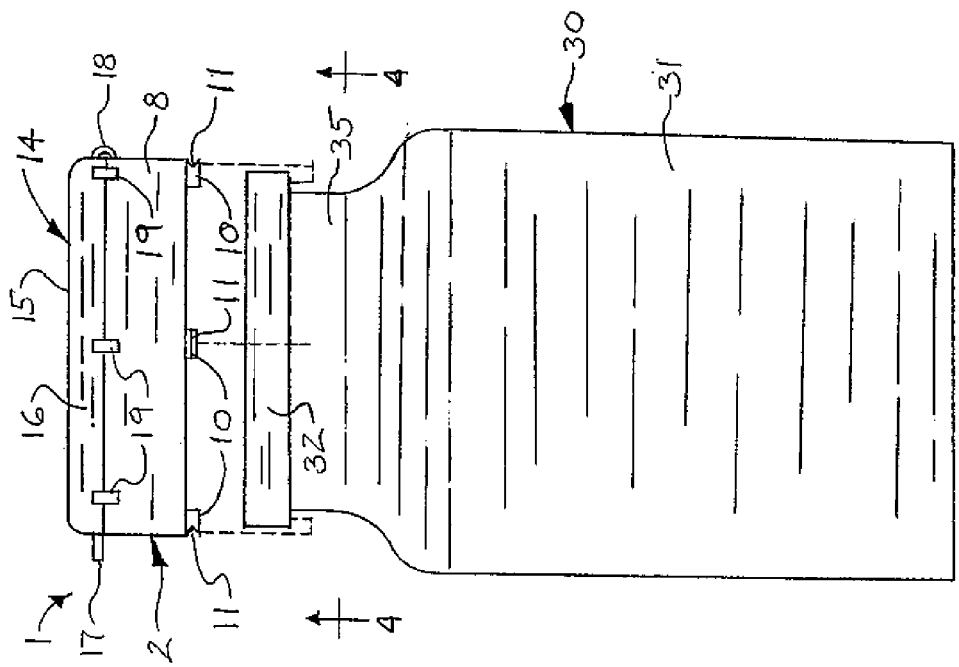
FIG. 1 is a side view of an illustrative embodiment of the self-disinfecting medication vial cap assembly, with an assembly base of the assembly fitted on a medication vial and an assembly cap of the assembly closed on the assembly base.
Figure 2:
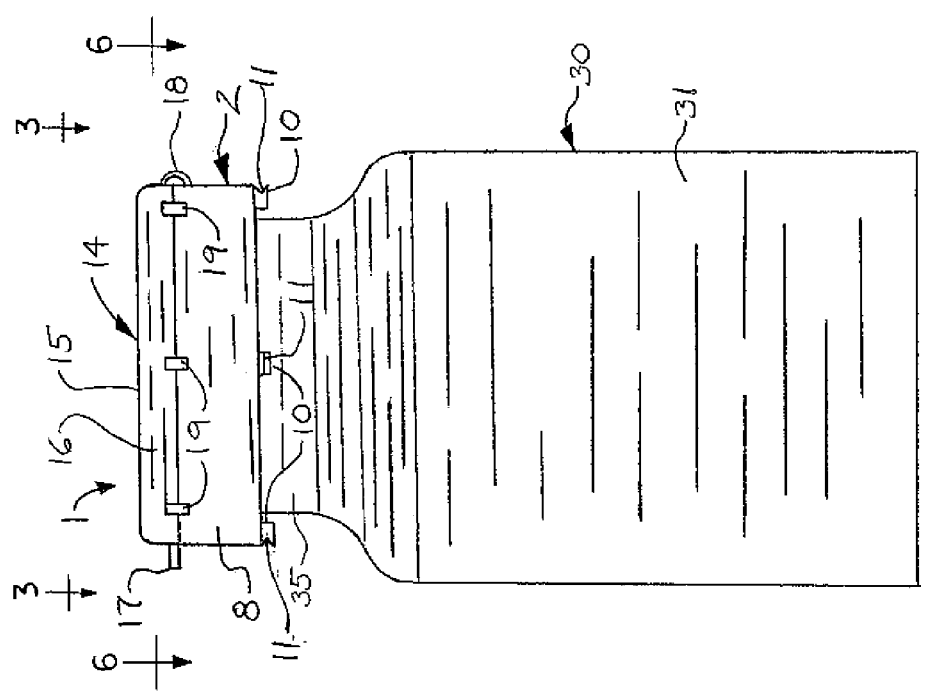
FIG. 2 is an exploded side view with the illustrative self-disinfecting medication vial cap assembly detached from the medication vial.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable users skilled in the art to practice the disclosure and are not intended to limit the scope of the claims. Moreover, the illustrative embodiments described herein are not exhaustive and embodiments or implementations other than those which are described herein and which fall within the scope of the appended claims are possible. Furthermore, there is no intention to be bound by any expressed or implied theory presented in the preceding technical field, background, brief summary or the following detailed description. Relative terms such as "upper", "lower", "top", "bottom" and "side" are used to aid in an understanding of the illustrative embodiments of the assembly and are not intended to be construed in a limiting sense. For purposes of description herein, the terms "upper", "lower", "top", "bottom" and "side" shall relate to the cap assembly as oriented in FIG. 1.

Referring initially to FIG. 10 of the drawings, an illustrative embodiment of the self-disinfecting medication vial cap assembly, hereinafter cap assembly, is generally indicated by reference numeral 1. As will be hereinafter described, the cap assembly 1 normally caps and seals a medication vial 30 which contains a supply of liquid medication 36. Upon opening, the cap assembly 1 self-disinfects to facilitate sterile insertion of a syringe needle 42 on a syringe 40 through the cap assembly 1 into the medication vial 30 to draw the medication 36 from the medication vial 30 into the syringe 40 and remove the syringe needle 42 from the medication vial 30 in a sterile manner. Thus, the cap assembly 1 ensures that the syringe needle 42 remains sterile upon subsequent application of the medication 36 to a patient.

Figure 4:
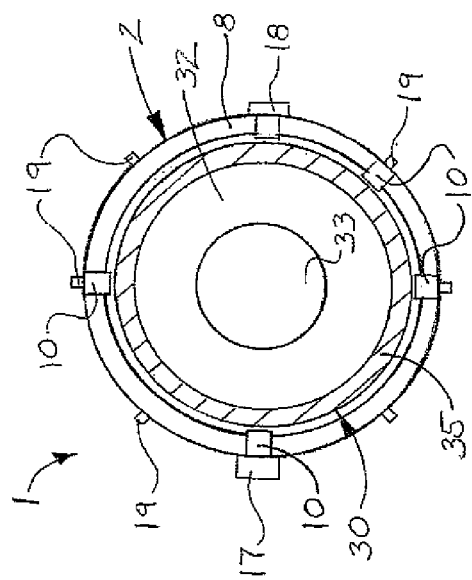
FIG. 4 is a bottom view, taken along section lines 4-4 in FIG. 2, of the illustrative self-disinfecting medication vial cap assembly, with the medication vial illustrated in cross-section.
Figure 3:
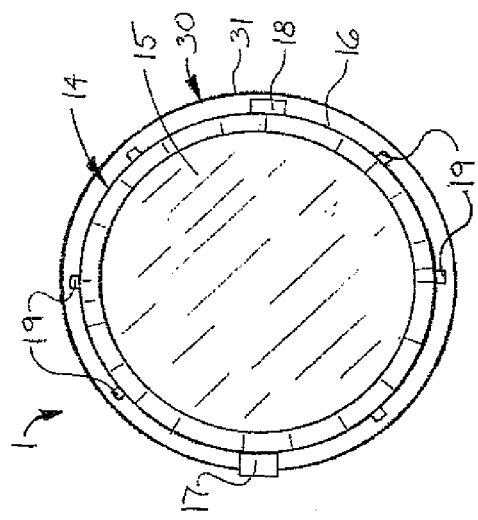
FIG. 3 is a top view of the illustrative self-disinfecting medication vial cap assembly, taken along viewing lines 3-3 in FIG. 1.
Figure 5:
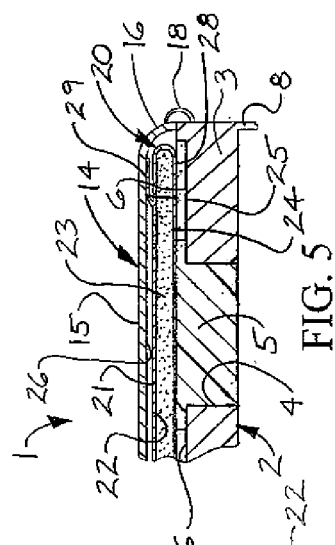
FIG. 5 is a cross-sectional view of a portion of the illustrative self-disinfecting medication vial cap assembly, with the assembly cap closed on the assembly base of the assembly and an intact antiseptic pouch in the assembly cap.
Figure 6:
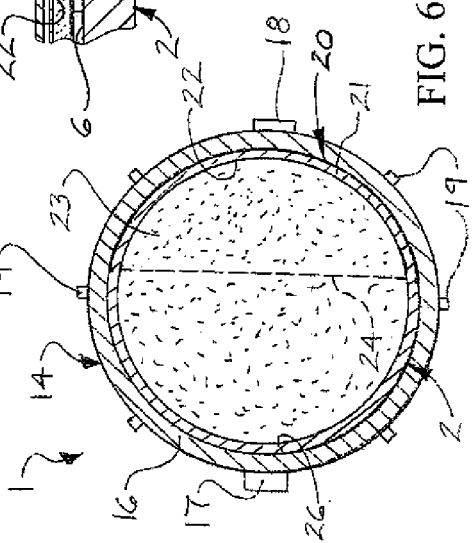
FIG. 6 is a cross-sectional view, taken along section lines 6-6 in FIG. 1, of the illustrative self-disinfecting medication vial cap assembly.
Figure 7:
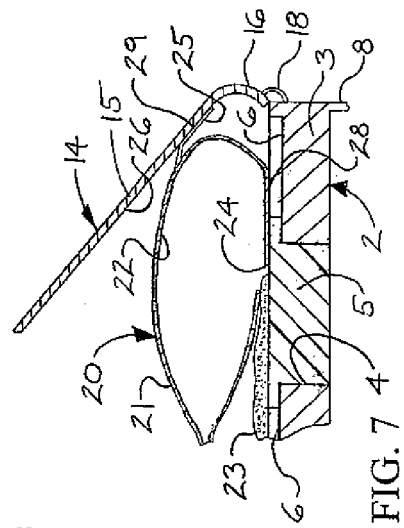
FIG. 7 is a cross-sectional view of the illustrative self-disinfecting medication vial cap assembly, with the assembly cap opened on the assembly base and antiseptic released from a ruptured antiseptic pouch in the assembly cap onto the assembly base to disinfect the assembly base upon opening of the assembly cap.

Referring next to FIGS. 1-7B of the drawings, the cap assembly 1 includes a needle-penetrable assembly base 2. The assembly base 2 is configured for attachment to the medication vial 30 according to the knowledge of those skilled in the art. In some embodiments, the assembly base 2 may include an assembly base body 3 which may be generally disc-shaped. As illustrated in FIGS. 5 and 7, a stopper opening 4 may extend through the assembly base body 3. A needle-penetrable assembly stopper 5 may be seated in the stopper opening 4 according to the knowledge of those skilled in the art. The assembly stopper 5 may include a medical-grade rubber, plastic, composite and/or other elastomeric or penetrable and liquid-impervious material which can be readily penetrated by the syringe needle 42 (FIG. 10) on the syringe 40 in typical application of the cap assembly 1, which will be hereinafter described. As further illustrated in FIGS. 5 and 7, in some embodiments, at least one antiseptic portal 6 may be provided in an interior or upper surface of the assembly base body 3. The antiseptic portal 6 may communicate with the stopper opening 4 for purposes which will be hereinafter described.

Figure 12:
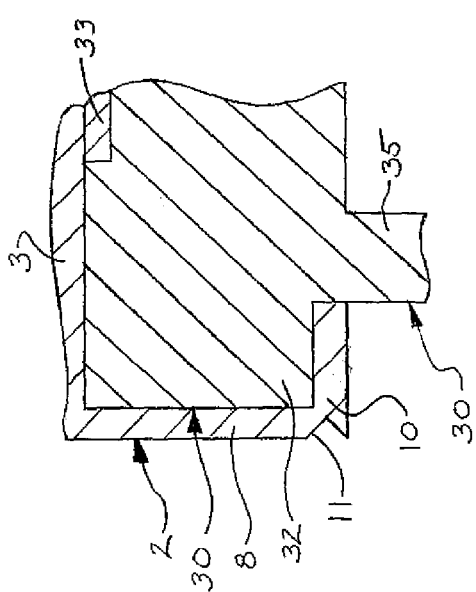
FIG. 12 is an enlarged sectional view of a typical junction between the assembly base of the illustrative medication vial cap assembly with a medication vial flange on the medication vial, more particularly illustrating engagement of an assembly attachment cleat on the assembly base with the medication vial flange on the medication vial.

An assembly base wall 8 may extend from the assembly base body 3. The assembly base wall 8 may be generally cylindrical in shape. At least one assembly attachment cleat 10 may protrude inwardly from a lower edge of the assembly base wall 8 for purposes which will be hereinafter described. As illustrated in FIG. 4, in some embodiments, multiple assembly attachment cleats 10 may be arranged in spaced-apart relationship to each other around the circumference of the assembly base wall 8. As illustrated in FIG. 12, in some embodiments, at least one cleat notch 11 may be provided in each assembly attachment cleat 10. The cleat notches 11 may render the respective assembly attachment cleats 10 sufficiently flexible for deformation and attachment to the medication vial 30. To render the cap assembly 1 tamper-proof, the size, configuration and placement of each cleat notch 11 may be selected such that each corresponding assembly attachment cleat 10 breaks off in the event that attempted removal of the cap assembly 1 is made.

An assembly cap 14 is provided on the assembly base 2. In some embodiments, the assembly cap 14 may include an assembly cap top panel 15. An assembly cap side wall 16 may extend from an outer or side edge of the assembly cap top panel 15. A cap interior 26 may be formed by the assembly cap top panel 15 and the assembly cap side wall 16. In some embodiments, a cap hinge 18 may pivotally attach the assembly cap side wall 16 of the assembly cap 14 to the assembly base body 3 of the assembly base 2. In other embodiments, the assembly cap 14 may be detachable from the assembly base 2.

As illustrated in FIGS. 7A and 7B, at least one frangible cap tab 19 may connect the assembly cap side wall 16 of the assembly cap 14 to the assembly base body 3 of the assembly base 2. In some embodiments, multiple frangible cap tabs 19 may be arranged in spaced-apart relationship to each other around the circumference of the assembly cap 14 and the assembly base 2. The cap tabs 19 may be fabricated in one piece with the assembly base 2 and the assembly cap 14 according to the knowledge of those skilled in the art. In some embodiments, each cap tab 19 may be scored with a tab score line 46 (FIG. 7A) to render the frangible connection between the assembly cap 14 and the assembly base 2. Accordingly, the cap tabs 19 normally secure the assembly cap 14 in the closed position on the assembly base 2, as illustrated in FIG. 5. Upon forceful application of upward lifting pressure to the assembly cap 14, the cap tabs 19 are broken or severed typically at the respective tab score lines 46, opening the assembly cap 14 on the assembly base 2. An assembly cap lift flange 17 may protrude outwardly from the assembly cap side wall 16 typically opposite the cap hinge 18 to aid in opening of the assembly cap 14. The assembly base 2 and the assembly cap 14 may include a medical-grade plastic, composite and/or other material which is consistent with the functional requirements of the cap assembly 1.

As illustrated in FIGS. 5-7, a antiseptic pouch 20 is provided in the cap interior 26 of the assembly cap 14. The antiseptic pouch 20 may include a breakable pouch membrane 21 which may be attached to an interior surface of the assembly base 2 typically along at least one base attachment point 28 and to an interior surface of the assembly cap 14 typically along at least one cap attachment point 29, as illustrated in FIGS. 5 and 7. In some embodiments, a membrane flap 25 may extend from the pouch membrane 21. The membrane flap 25 may be attached to the interior surface of the assembly cap 14 along at least one cap attachment point 29. The base attachment point 28 and the cap attachment point 29 may include glue, adhesive, heat seals, mechanical fasteners and/or other suitable attachment technique which is known by those skilled in the art and suitable for the purpose of securely attaching the pouch membrane 21 and the membrane flap 25 to the assembly base 2 and the assembly cap 14, respectively. The antiseptic pouch 20 has a pouch interior 22. A medical-grade antiseptic 23 is provided in the pouch interior 22. The antiseptic 23 may include any type of solution which may be used to disinfect medical instruments or surfaces in medical applications. For example and without limitation, in some embodiments, the antiseptic 23 may include isopropyl alcohol. The antiseptic 23 is suitable for disinfecting the interior surfaces of the assembly base body 3 and the assembly stopper 5 upon rupture of the antiseptic pouch 20 and release of the antiseptic 23 from the ruptured antiseptic pouch 20, as will be hereinafter described. The pouch membrane 21 may include foil, plastic, paper and/or other rupturable or breakable material.

In some embodiments, at least one membrane perforation 24 may be provided in the pouch membrane 21. As illustrated in FIG. 5, the membrane perforation 24 may be generally above or adjacent to the upper or interior surface of the assembly stopper 5 in the cap interior 26 of the assembly cap 14. In the closed position of the assembly cap 14 on the assembly base 2, illustrated in FIG. 5, the membrane perforation 24 remains intact. Upon opening of the assembly cap 14 on the assembly base 2, as illustrated in FIG. 7, the assembly cap 14 pulls upwardly on the membrane flap 25. In turn, the membrane flap 25 pulls upwardly on the pouch membrane 21, rupturing the pouch membrane 21 along the perforation 24. Consequently, the antiseptic 23 is released from the ruptured pouch membrane 21 at the broken perforation 24 and onto the assembly stopper 5 in the assembly base 2. Thus, the antiseptic 23 disinfects the assembly stopper 5 preparatory to insertion of the syringe needle 42 (FIG. 10) through the assembly stopper 5 to draw the medication 36 from the medication vial 30 into the syringe 40, as will be hereinafter further described.

Referring next to FIGS. 8-12 of the drawings, in typical application, the cap assembly 1 seals a medication vial 30 which contains a supply of liquid medication 36 typically for the purpose of injection into a patient. The medication vial 30 may have a conventional design with a cylindrical medication vial wall 31 forming a medication vial interior 34 which contains the medication 36. A medication vial neck 35 may extend from the medication vial wall 31. A flared medication vial flange 32 may protrude outwardly from the medication vial neck 35. A medication vial stopper 33 is seated in a stopper opening (not numbered) which extends through the medication vial flange 32. The medication 36 is contained in the medication vial interior 34.

Figure 11C:
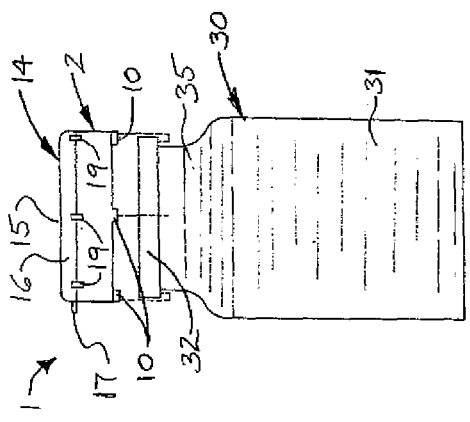
FIG. 11C is a side view of the medication vial illustrated in FIGS. 11A and 11B, more particularly illustrating placement of the illustrative medication vial cap assembly on the medication vial.
Figure 11B:
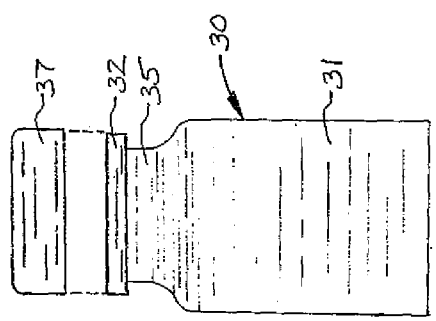
FIG. 11B is a side view of the medication vial illustrated in FIG. 11A, more particularly illustrating detachment of the vial cap from the medication vial preparatory to placement of the medication vial cap assembly on the medication vial.
Figure 11A:
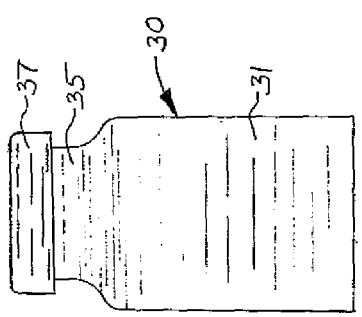
FIG. 11A is a side view of a typical medication vial fitted with a conventional vial cap prior to removal of the vial cap and placement of the medication vial cap assembly on the vial.

As illustrated in FIG. 11A, the medication vial 30 may be commercially available with a vial cap 37 attached to the medication vial flange 32 for sealing purposes. In some applications, an end user (not illustrated) may initially detach the vial cap 37 from the medication vial flange 32, as illustrated in FIG. 11B, and then place the medication vial cap assembly 1 on the medication vial flange 32, as illustrated in FIG. 11C. In other applications, the medication vial assembly 1 may be secured in place on the medication vial flange 32 by a manufacturer.

The assembly base 2 may be attached to the medication vial flange 32 with the assembly base wall 8 extending around the exterior surface and the assembly attachment cleats 10 engaging the lower surface of the medication vial flange 32, as particularly illustrated in FIG. 12. The cleat notch 11 in each assembly attachment cleat 10 may render the attachment cleats 10 sufficiently flexible to facilitate placement of the assembly attachment cleats 10 to the medication vial flange 32. Accordingly, as illustrated in FIGS. 8-10, the assembly stopper 5 in the assembly base 2 aligns or registers with the underlying medication vial stopper 33 in the medication vial flange 32. The cap tabs 19 seal the assembly cap 14 in the closed position on the assembly base 2. Each cap tab 19 may be fabricated in one piece with the assembly base wall 8 of the assembly base 2 and the assembly cap side wall 16 of the assembly cap 14 according to the knowledge of those skilled in the art. In some embodiments, each cap tab 19 may be scored with the tab score line 46 (FIG. 7A) to render the frangible connection between the assembly cap 14 and the assembly base 2.

As illustrated in FIG. 8, the assembly cap 14 normally remains closed on the assembly base 2 to seal the cap interior 26. Accordingly, in the closed position of the assembly cap 14, the membrane perforation 24 (FIGS. 5-7) remains intact. When it is desired to draw a quantity of the medication 36 into a syringe 40, as illustrated in FIG. 10, for subsequent injection into a patient, the assembly cap 14 is pivoted from the closed position illustrated in FIG. 8 to the open position illustrated in FIGS. 9 and 10 typically via the cap hinge 18 by application of upward pressure to the assembly cap lift flange 17 on the assembly cap 14. As the assembly cap 14 pivots to the open position on the assembly base 2, the assembly cap 14 pulls upwardly on the membrane flap 25 which pulls and ruptures the pouch membrane 21 typically along the perforation 24, as was heretofore described with respect to FIG. 7. Consequently, the antiseptic 23 is released from the ruptured pouch membrane 21 at the broken perforation 24 and onto the assembly stopper 5 in the assembly base 2, as illustrated in FIG. 9. Thus, the antiseptic 23 disinfects the assembly stopper 5. As illustrated in FIG. 10, the syringe needle 42 on the syringe 40 is inserted through the assembly stopper 5 in the assembly base 2 of the cap assembly 1 and through the underlying medication vial stopper 33 in the medication vial flange 32 of the medication vial 30 into the medication 36. The syringe plunger 43 is withdrawn from the syringe barrel 41 of the syringe 40 to draw the medication 36 from the medication vial 30 through the syringe needle 42 into the syringe barrel 41. The syringe needle 42 is withdrawn from the medication vial stopper 33 and the assembly stopper 5 and the medication 36 is typically injected into a patient. The assembly cap 14 can be closed on the assembly base 2 for subsequent withdrawal of the medication 36 in a similar manner, or alternatively, may be discarded.

While illustrative embodiments of the disclosure have been described above, it will be recognized and understood that various modifications can be made and the appended claims are intended to cover all such modifications which may fall within the spirit and scope of the disclosure.

What is claimed is:

1. A self-disinfecting medication vial cap assembly for a medication vial, comprising:
   a needle-penetrable assembly base configured for attachment to the medication vial;
   an assembly cap carried by the assembly base, the assembly base and the assembly cap having a cap interior and the assembly cap positional between closed and open positions;
   a rupturable antiseptic pouch attached to the assembly base and the assembly cap in the cap interior;
   an antiseptic contained in the antiseptic pouch;
   the antiseptic pouch remains intact in the closed position of the assembly cap; and
   the antiseptic pouch ruptures and the antiseptic is discharged onto the assembly base upon and coincident with movement of the assembly cap from the closed position to the open position.

2. The self-disinfecting medication vial cap assembly of claim 1 wherein the assembly cap is pivotally carried by the assembly base.

3. The self-disinfecting medication vial cap assembly of claim 1 further comprising at least one frangible cap tab connecting the assembly cap to the assembly base in the closed position.

4. The self-disinfecting medication vial cap assembly of claim 1 further comprising at least one assembly attachment cleat carried by the assembly base, the at least one assembly attachment cleat configured to attach the assembly base to the medication vial.

5. The self-disinfecting medication vial cap assembly of claim 4 further comprising at least one cleat notch in the at least one assembly attachment cleat.

6. The self-disinfecting medication vial cap assembly of claim 1 wherein the antiseptic pouch comprises a rupturable pouch membrane having a pouch interior, and wherein the antiseptic is contained in the pouch interior.

7. The self-disinfecting medication vial cap assembly of claim 1 wherein the assembly base comprises an assembly base body, a stopper opening in the assembly base body, a needle-penetrable assembly stopper seated in the stopper opening and an assembly base wall extending from the assembly base body.

8. The self-disinfecting medication vial cap assembly of claim 7 further comprising at least one antiseptic portal in the assembly base body, the at least one antiseptic portal communicating with the stopper opening.

9. A self-disinfecting medication vial cap assembly for a medication vial, comprising:
- a needle-penetrable assembly base configured for attachment to the medication vial;
- an assembly cap carried by the assembly base, the assembly base and the assembly cap having a cap interior and the assembly cap positional between closed and open positions; and
- a rupturable antiseptic pouch attached to the assembly base and the assembly cap in the cap interior, the antiseptic pouch including:
  - a rupturable pouch membrane having a pouch interior;
  - at least one membrane perforation in the pouch membrane; and
  - an antiseptic contained in the antiseptic pouch;
- the antiseptic pouch remains intact in the closed position of the assembly cap; and
- the antiseptic pouch ruptures and the antiseptic is discharged onto the assembly base upon movement of the assembly cap from the closed position to the open position.

10. The self-disinfecting medication vial cap assembly of claim 9 wherein the assembly cap is pivotally carried by the assembly base.

11. The self-disinfecting medication vial cap assembly of claim 9 further comprising at least one frangible cap tab connecting the assembly cap to the assembly base in the closed position.

12. The self-disinfecting medication vial cap assembly of claim 9 further comprising at least one assembly attachment cleat carried by the assembly base, the at least one assembly attachment cleat configured to attach the assembly base to the medication vial.

13. The self-disinfecting medication vial cap assembly of claim 12 further comprising at least one cleat notch in the at least one assembly attachment cleat.

14. The self-disinfecting medication vial cap assembly of claim 9 wherein the antiseptic comprises isopropyl alcohol.

15. The self-disinfecting medication vial cap assembly of claim 9 wherein the assembly base comprises an assembly base body, a stopper opening in the assembly base body, a needle-penetrable assembly stopper seated in the stopper opening and an assembly base wall extending from the assembly base body.

16. The self-disinfecting medication vial cap assembly of claim 15 further comprising at least one antiseptic portal in the assembly base body, the at least one antiseptic portal communicating with the stopper opening.

17. A self-disinfecting medication vial cap assembly for a medication vial, comprising:
- a needle-penetrable assembly base including:
  - a generally disc-shaped assembly base body;
  - a stopper opening in the assembly base body;
  - a needle-penetrable assembly stopper seated in the stopper opening;
  - an assembly base wall extending from the assembly base body; and
  - a plurality of assembly attachment cleats carried by the assembly base wall, the assembly attachment cleats configured for attachment to the medication vial;
- an assembly cap carried by the assembly base, the assembly base and the assembly cap having a cap interior and the assembly cap positional between closed and open positions;
- a plurality of frangible cap tabs connecting the assembly cap to the assembly base in the closed position; and
- a rupturable antiseptic pouch attached to the assembly base in the cap interior, the antiseptic pouch including:
  - a rupturable pouch membrane having a pouch interior;
  - a membrane flap connecting the pouch membrane to the assembly cap;
  - at least one membrane perforation in the pouch membrane; and
  - an antiseptic contained in the antiseptic pouch;
- the antiseptic pouch remains intact in the closed position of the assembly cap; and
- the antiseptic pouch ruptures and the antiseptic is discharged onto the assembly base upon movement of the assembly cap from the closed position to the open position.

18. The self-disinfecting medication vial cap assembly of claim 17 wherein the assembly cap is pivotally carried by the assembly base.

19. The self-disinfecting medication vial cap assembly of claim 17 further comprising at least one cleat notch in each of the plurality of assembly attachment cleats.

20. The self-disinfecting medication vial cap assembly of claim 17 further comprising at least one antiseptic portal in the assembly base body, the at least one antiseptic portal communicating with the stopper opening.

* * * * *